(12) United States Patent
Thompson et al.

(10) Patent No.: US 8,428,398 B2
(45) Date of Patent: Apr. 23, 2013

(54) HAND-HELD PORTABLE MICROARRAY READER FOR BIODETECTION

(75) Inventors: Deanna Lynn Thompson, Orangevale, CA (US); Matthew A. Coleman, Oakland, CA (US); Stephen M. Lane, Oakland, CA (US); Dennis L. Matthews, Gold River, CA (US); Joanna Albala, Stockton, CA (US); Sebastian Wachsmann-Hogiu, Sacramento, CA (US)

(73) Assignees: Lawrence Livermore National Security, LLC, Livermore, CA (US); The Regents of the University of California, Oakland, CA (US)

( * ) Notice: Subject to any disclaimer, the term of this patent is extended or adjusted under 35 U.S.C. 154(b) by 297 days.

(21) Appl. No.: 12/826,215

(22) Filed: Jun. 29, 2010

(65) Prior Publication Data

US 2011/0188782 A1 Aug. 4, 2011

Related U.S. Application Data

(60) Provisional application No. 61/300,353, filed on Feb. 1, 2010.

(51) Int. Cl.
*G06K 9/22* (2006.01)
(52) U.S. Cl.
USPC .......................................... 382/313; 348/294
(58) Field of Classification Search .................. None
See application file for complete search history.

(56) References Cited

U.S. PATENT DOCUMENTS

| | | | |
|---|---|---|---|
| 6,818,435 B2 | 11/2004 | Carvalho et al. | |
| 7,033,747 B2 | 4/2006 | Gordon | |
| 7,141,416 B2 | 11/2006 | Krutzik | |
| 2003/0003464 A1 | 1/2003 | Phan et al. | |
| 2007/0098596 A1 | 5/2007 | Fries et al. | |
| 2009/0309967 A1* | 12/2009 | Kim et al. | 348/143 |

FOREIGN PATENT DOCUMENTS

GB 2341924 A 3/2000

OTHER PUBLICATIONS

David B. Fenner, David I. Rosen, Anthony A. Ferrante, Amy E. Stevens, Chad E. Bigelow, and Steven J. Davis, "Development of a First-Responder Fluorescence Reader for Microarray Cytokine Assay of Human Immune Response to Disease", 2007, Material Research Society, Mater. Res. Soc. Symp. Proc. vol. 1004.*

(Continued)

*Primary Examiner* — Andrew W Johns
*Assistant Examiner* — Siamak Harandi
(74) *Attorney, Agent, or Firm* — Eddie E. Scott (57) ABSTRACT

A hand-held portable microarray reader for biodetection includes a microarray reader engineered to be small enough for portable applications. The invention includes a high-powered light-emitting diode that emits excitation light, an excitation filter positioned to receive the excitation light, a slide, a slide holder assembly for positioning the slide to receive the excitation light from the excitation filter, an emission filter positioned to receive the excitation light from the slide, a lens positioned to receive the excitation light from the emission filter, and a CCD camera positioned to receive the excitation light from the lens.

16 Claims, 10 Drawing Sheets

OTHER PUBLICATIONS

Sergei G. Bavykin, James P. Akowski, Vladimir M. Zakhariev, Viktor E. Barsky, Alexander N. Perov, and Andrei D. Mirzabekov, "Portable System for Microbial Sample Preparation and Oligonucleotide Microarray Analysis", Feb. 2001, Applied and Environmental Microbiology, pp. 922-928.*

Deanna L. Thompson, "An Adaptable; Portable Microarray Reader for Biodetection". Sensors 2009, 9, 2524-2537; doi: 10.3390/s90402524. Sensors, ISSN 1424-8220. Published Apr. 14, 2009.

* cited by examiner

| PBS Buffer | PBS Buffer | Cy3 SA 10μg/ml | Cy3 SA 10μg/ml | Cy3 SA 10μg/ml | Cy3 SA 1μg/ml | Cy3 SA 1μg/ml | Cy3 SA 1μg/ml |
|---|---|---|---|---|---|---|---|
| Cy3 AM 100μg/ml | Cy3 AM 100μg/ml | Cy3 AM 10μg/ml | Cy3 AM 10μg/ml | Cy3 AM 10μg/ml | Cy3 AM 1μg/ml | Cy3 AM 1μg/ml | Cy3 AM 1μg/ml |
| Cy5 AR 100μg/ml | Cy5 AR 100μg/ml | Cy5 AR 10μg/ml | Cy5 AR 10μg/ml | Cy5 AR 10μg/ml | Cy5 AR 1μg/ml | Cy5 AR 1μg/ml | Cy5 AR 1μg/ml |
| Cy3 BTAM 2μg/ml | Cy3 BTAM 0.2μg/ml | Cy3 BTAM 0.2μg/ml | Cy3 BTAM 0.2μg/ml | Cy3 BTAM 0.2μg/ml | Cy3 BTAM 0.02μg/ml | Cy3 BTAM 0.02μg/ml | Cy3 BTAM 0.02μg/ml |
| Cy3 BTAG 2μg/ml | Cy3 BTAG 0.2μg/ml | Cy3 BTAG 0.2μg/ml | Cy3 BTAG 0.2μg/ml | Cy3 BTAG 0.2μg/ml | Cy3 BTAG 0.02μg/ml | Cy3 BTAG 0.02μg/ml | Cy3 BTAG 0.02μg/ml |

HAND-HELD PORTABLE MICROARRAY READER FOR BIODETECTION

CROSS-REFERENCE TO RELATED APPLICATIONS

The present application claims benefit under 35 U.S.C. §119(e) of U.S. Provisional Patent Application No. 61/300,353 filed Feb. 1, 2010 entitled "Hand-held Portable Microarray Reader," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to sample analysis and more particularly to a hand-held portable microarray reader.

2. State of Technology

U.S. Pat. No. 6,818,435 to Bruce L. Cavalho et al for microfluidics devices and methods for performing cell based assays provides the state of technology information set out below. The disclosure of U.S. Pat. No. 6,818,435 is incorporated herein in its entirety by this reference.

Recent developments in a variety of investigational and research fields have created a need for improved methods and apparatus for performing analytical, particularly bioanalytical assays at microscale (i.e., in volumes of less than 100 µL). In the field of pharmaceuticals, an increasing number of potential drug candidates require assessment of their biological function. As an example, the field of combinatorial chemistry combines various structural sub-units with differing chemical affinities or configurations into molecules; in theory, a new molecule having potentially unique biochemical properties can be created for each permutation of the sub-units. In this way, large libraries of compounds may be synthesized from relatively small numbers of constituents, each such compound being a potential drug lead compound of usually unknown biological activity and potency. Similarly, increasingly large numbers of targets for these putative therapeutic compounds are being discovered, many as a result of the growing information derived from such large-scale biological research as the sequencing of the human genome.

U.S. Pat. No. 7,033,747 to John Francis Gordon for multi-parameter assays including analysis discs and methods relating thereto provides the state of technology information set out below. The disclosure of U.S. Pat. No. 7,033,747 is incorporated herein in its entirety by this reference.

There is a significant need to make diagnostic assays and forensic assays of all types faster and more local to the end-user. Ideally, clinicians, patients, investigators, the military, other health care personnel, and consumers should be able to test themselves for the presence of certain factors or indicators in their systems, and for the presence of certain biological material at a crime scene or on a battlefield. At present, there are a number of silicon-based chips with nucleic acids and/or proteins attached thereto, which are commercially available or under development, for performing biomedical, chemical, or biochemical assays. These chips are not for use by the end-user, or for use by persons or entities lacking very specialized expertise and expensive equipment. It is an object of the present invention to obviate or mitigate at least one of these disadvantages by use of a relatively inexpensive assay system that can be used by the end user without specialized training.

U.S. Pat. No. 7,141,416 to Siegfried Richard Krutzik for multi-purpose optical analysis optical bio-disc for conducting assays and various reporting agents for use therewith provides the state of technology information set out below. The disclosure of U.S. Pat. No. 7,141,416 is incorporated herein in its entirety by this reference.

The detection and quantification of analytes in the blood or other body fluids are essential for diagnosis of diseases, elucidation of the pathogenesis, and for monitoring the response to drug treatment. Traditionally, diagnostic assays are performed in laboratories by trained technicians using complex apparatus. Performing these assays is usually time-consuming and costly. Thus, there is a significant need to make diagnostic assays and forensic assays of all types faster and more local to the end-user. Ideally, clinicians, patients, investigators, the military, other health care personnel, and consumers should be able to test themselves for the presence of certain risk factors or disease indicators in their systems, and to test for the presence of certain biological material at a crime scene or on a battlefield. At present, there are a number of medical diagnostic, silicon-based, devices with nucleic acids and/or proteins attached thereto that are commercially available or under development. These chips are not for use by the end-user, or for use by persons or entities lacking very specialized expertise and expensive equipment.

United States Published Patent Application No. 2003/0003464 by Brigitte C. Phan for dual bead assays including optical biodiscs and methods relating thereto provides the state of technology information set out below. The disclosure of United States Published Patent Application No. 2003/0003464 is incorporated herein in its entirety by this reference.

There is a significant need to make diagnostic assays and forensic assays of all types faster and more local to the end-user. Ideally, clinicians, patients, investigators, the military, other health care personnel and consumers should be able to test themselves for the presence of certain factors or indicators in their systems, for the presence of certain biological material at a crime scene or on a battlefield. At present, there are a number of silicon based chips with nucleic acids and/or proteins attached thereto which are commercially available or under development. These chips are not for use by the end-user, or for use by persons or entities lacking very specialized expertise and expensive equipment.

UK Patent Application No. GB 2,341,924 A for a microfluidic device provides the state of technology information set out below. The disclosure of UK Patent Application No. GB 2,341,924 A is incorporated herein in its entirety by this reference.

It has now been found that microfluidic devices can be prepared in which fluid flow may be controlled by having different surfaces of the substrate forming the device having different surface characteristics. By "microfluidic devices" is meant devices that can handle microvolumes of reagents, for example samples of less than 9 μl, suitably less than 500 nl and preferably between 1 and 10 nl, may be introduced into the device. By "fluid" is meant dry powders and liquids, including suspensions of particulates in liquids.

United States Published Patent Application No. 2007/0098596 by David P. Fries and Matthew Smith of the University of South Florida for a handheld microarray reader provides the state of technology information set out below. The disclosure of United States Published Patent Application No. 2007/0098596 is incorporated herein in its entirety by this reference.

Microarray readers are devices used in biotechnology and other clinical and research settings. The readers utilize a "microarray", such as can be made by putting a large number of tiny droplets of DNA, including cDNA, and proteins on glass slide or in a multi-well plate. Short pieces of DNA, called probes, are then applied to the DNAs on the slide. Alternatively, in the case of a protein, a molecule that selectively binds a protein of interest, such as an antibody, or fragment thereof, is applied to the sample and allowed to bind under appropriate conditions for specific binding to a target sample. Typically, the probes are fluorescent or luminescent, so they light up when short wavelength light is shone on them (the probes can also be labeled with other substances to reflect or otherwise emanate light when they are scanned). Microarrays can be used, for example, to study how large numbers of genes interact with each other (genes are made of DNA), or how a cell is able to simultaneously control vast numbers of genes.

The probes hybridize to targets on the microarray based upon complentarity under the stringency of the application. The microarrays are then put into a scanning microarray reader that measures the brightness of each fluorescent dot: the brighter the dot, the more probe, and thus the more target. DNA or other biological material, is present, thus allowing quantification of the sample based upon intensity against standards.

Microarrays can be used, for example, to study genomic content, how large numbers of genes interact with each other (genes are made of DNA), or how a cell is able to simultaneously control vast numbers of genes (expression patterns). Different types of microarrays include, but are not limited to, eDNA arrays, oligonucleotide arrays and protein arrays.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a hand-held portable microarray reader for biodetection. In one embodiment the present invention provides a hand-held portable microarray reader based on LEDs, lens, and CCD camera. The hand-held portable microarray reader for biodetection is designed for quantitative detection of the emission of light or other indicia from a labeled biological sample. The present invention provides a small portable prototype fluorescence reader capable of running on solar, battery pack, or USB connection for field diagnosis. The present invention is useful for clinical or triage settings for any biodetection scenario for capturing nucleic acids or proteins. Immediate applications include use in biodosimetry, pathogen analysis and environmental detection.

In one embodiment the present invention provides a microarray reader engineered to be small enough for portable applications. A prototype was built that is 19 cm in length with a base of 6.5 cm×5 cm and was built for less than $3,000. Excitation is provided by an LED source and the device also contains a focusing lens and CCD for detection. One embodiment the present invention includes a high-powered light-emitting diode that emits excitation light, an excitation filter positioned to receive the excitation light, a slide, a slide holder assembly for positioning the slide to receive the excitation light from the excitation filter, an emission filter positioned to receive the excitation light from the slide, a lens positioned to receive the excitation light from the emission filter, and a CCD camera positioned to receive the excitation light from the lens.

The present invention has use as point-of-care molecular diagnostics and as a bio-detector for homeland security. The DNA microarray market in the U.S. is growing. Additional growth is expected due to developments for molecular diagnostics applications.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF SPECIFIC EMBODIMENTS

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Antibody-based immunoassays are currently the most commonly used tools to measure biomarkers in patient samples. Since their first use in the 1950s, newer and more efficient antibodies and other affinity reagents have been created to improve assay sensitivity. The development of antibody microarrays has played an increasingly important role in biology and medicine, and tremendous progress has been made in the development of new array-based technology platforms for biological research. Microarrays offer several distinct advantages over conventional analytical technologies, including requiring only small sample and reagent volumes, and offering high-throughput parallel analysis. This technology has been used successfully to detect and quantify specific target proteins in complex mixtures such as clinical samples.

New diagnostic tests, such as microarray-based assays for breast cancer or for autoimmune diseases, have the potential to dramatically change the face of medicine. However, the mainstream medical community is often slow to adopt new technologies. Some of the reluctance is due to the cost of new technology, unwieldy equipment unsuitable for an office setting, or lack of time to learn to use a complicated system. There is, therefore, an increasing demand for simple, point-of-care (FOC) diagnostic assays and readers capable of providing rapid, sensitive and quantitative results.

POC integrated systems possess the ability to process clinical samples for a number of different types of biomarkers in a variety of settings, such as clinical laboratories, patients' bedsides, and doctors' offices. Automation of clinical diagnostic tests is also highly desirable as it would improve the efficiency of the laboratory and reproducibility of the testing procedure by eliminating human error. This is especially necessary in situations where assays need to be performed without the use of a laboratory or trained individuals. In addition, implementation of POC technologies should be, by their very nature, low cost.

Microarray assays can be adapted to fit fully on a standard microscope slide for POC applications. After a brief incubation period, the only equipment needed to analyze the results of a preprinted assay is a microarray reader and a simple image processor. However, current microarray laser scanners/readers cost tens of thousands of dollars, are space prohibitive, and require a trained operator.

Ideally a small, inexpensive, and specialized reader would complement the slide-based assay. One of the challenges in creating such a reader is miniaturizing the light source without drastically reducing the excitation light. A portable microarray imager was developed that utilizes a small laser diode, but their use of a film-based camera precluded rapid analysis of the array. Another group later demonstrated a digital portable microarray reader using an ultra-bright LED for excitation, but their system was designed for laboratory use rather than as a clinical prototype.

Although both systems were smaller than traditional scanners, they cannot be easily stored and handled in doctors' offices, and neither group provided comparative validation of their prototypes using a commercial scanner. A small biosensor platform was developed that overcomes some of these barriers, but lacks the ability to easily adapt to new sizes or shapes of fluorescent patterns.

Applicants' invention provides a new alternative to microarray scanners that would meet the needs of the market. By addressing some of the drawbacks of commercial scanners, such as size, cost, and complexity, Applicants' specialized device will appeal to those looking for POC microarray solutions. While the handheld microarray reader described here lacks some of the features and functions of the larger laser scanners, its small and minimalistic design makes it ideal for specialized uses such as rapid diagnosis in medical clinics and other POC settings. Additionally, when combined with a lateral flow assay such as previously described, the sample does not need to be sent to a separate laboratory for processing. Although Applicants' reader does not automatically scan a full slide, we believe that Applicants' field of view is sufficient to accommodate the typical number of biomarkers to be used for a single POC assay, thus easily fitting within one image. Furthermore, in recognition that accuracy is of the utmost importance for acceptance by medical providers, we provide here a direct comparison of Applicants' handheld imager to a commercial scanner.

One embodiment of the present invention is an inexpensive handheld microarray reader for use with a standard array printed on modified glass slides. Measuring only seven inches in length and two and a half inches at the base, this hand-held array reader can easily be applied in a triage or clinical setting. The minimalistic design fulfills its purpose while reducing the risk of malfunction, and is easily adaptable for different excitation and emission spectra. Additionally, the image is digital, allowing for easier image processing compared to previous film-based portable microarray readers. Microarray image processing has become an important field of research to produce novel tools amenable to both field and clinical settings.

Applicants' hand-held portable microarray reader apparatus for analyzing a sample provides advantage over prior art devices. Some of the advantages are described below.

1. Applicants' is not limited to use with arrays;
2. Applicants' is not and does not use "night vision" technology;
3. Applicants' does not intensify or enhance the signal prior to the camera;
4. Applicants' does not have a specific or controllable heating element (although the LED does put out a lot of heat, that is not an intended or generally useful design element);
5. Although the focus of Applicants' is on fluorescence, by using different filters Applicants' is not actually limited to fluorescence imaging (can be white light, for example);
6. Applicants' does not have a light-modulating controller;
7. Applicants' is back-illuminated, which is very distinctive from any other microarray readers;
8. Applicants' has flexible utility, such as described by changing the filters; sample types; or on-board, customizable, application-specific programming; and
9. Applicants' basic design is much simpler with fewer components.

Figure 1:
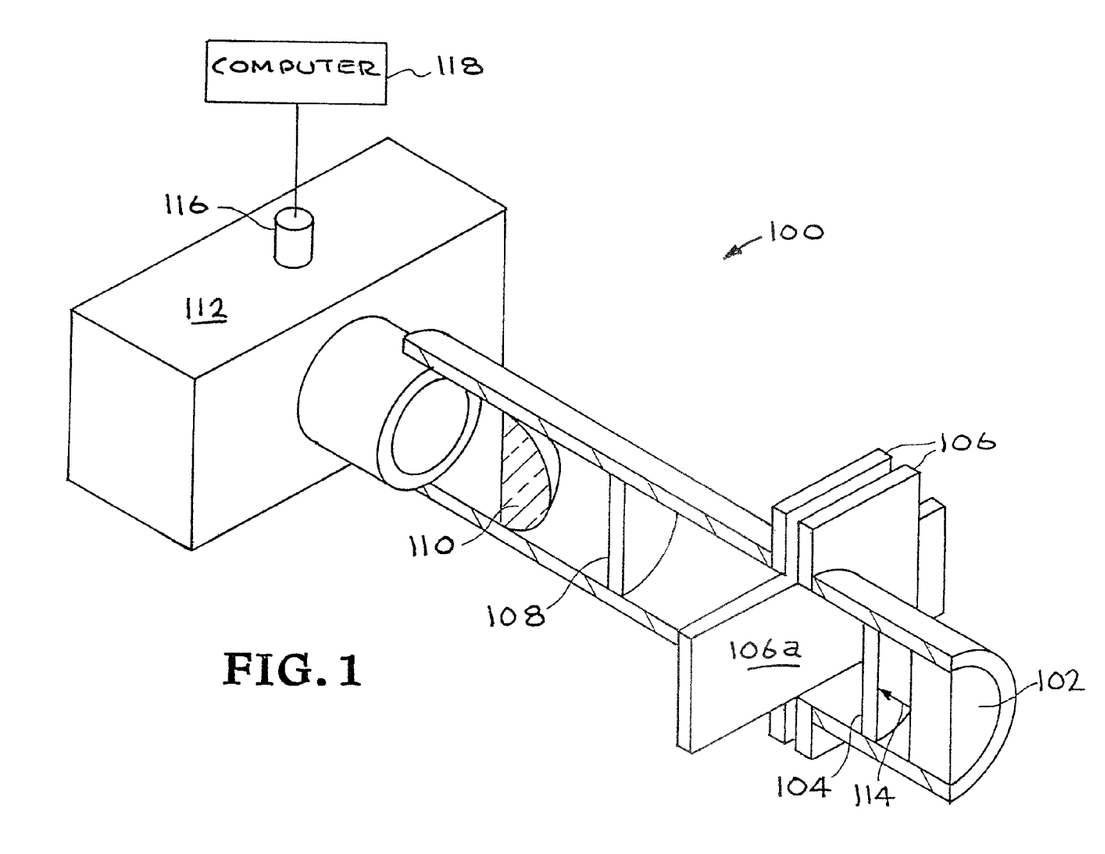
FIG. 1 is a 3D schematic illustration of a hand-held microarray reader for biodetection constructed in accordance with the present invention.

Referring now to the drawings and in particular to FIG. 1, a 3D schematic illustration of a hand-held microarray reader for biodetection constructed in accordance with the present invention is illustrated. The hand-held microarray reader for biodetection is designated generally by the reference numeral 100. The hand-held microarray reader for biodetection 100 combines simplicity with multifunctionality. The hand-held microarray reader for biodetection 100 includes the following structural elements: a high-powered light-emitting diode (LED) 102, excitation filters 104, a slide 106a, slide holder assembly 106, emission filters 108, lens 110, camera 112, USB connection 116, and laptop computer 118.

The high-powered light-emitting diode (LED) 102 is a semiconductor diode that emits light when a voltage is applied to it and that is used in the hand-held microarray reader for biodetection 100. The high-powered light-emitting diode (LED) 102 is defined as an ultra-bright LED, powered at 3.3 V, with a peak wavelength of 530 nm with a range of 520-550 nm, and the power being approximately 80 mW. The high-powered light-emitting diode (LED) 102 provides illumination to back illuminate the slide 106a.

The LED 102 provides the excitation light 114. The excitation light 114 is narrowed by the set of excitation filters 104 before illuminating the field of view with approximately 4 mW of 530 nm light. This translates to roughly $16 \times 10^{15}$ photons per second per square centimeter, or $3 \times 10^{12}$ photons per second per microarray spot. The light propagating in the forward direction then passes through another set of filters, emission filters 108, so that only the fluorescent light from the microarray is focused onto the detector camera 112. The high inherent numerical aperture (NA=0.45) of the focusing lens 110 allows for high collection efficiency. From the CCD detector camera 112, a 16-bit fluorescence image is captured. The image can be saved via USB connection 116 to a laptop computer 118 for image analysis and processing. With a field of view of approximately 7.5×10 mm, a 30×40 array of spots spaced by 250 μm spot-to-spot both horizontally and vertically can be visualized in one image by the hand-held microarray reader for biodetection 100.

The hand-held microarray reader for biodetection 100 provides hand-held portable microarray reader based on LEDs, lens and CCD camera. Measuring only 19 cm in length with a footprint of 6.5 cm×5 cm, the imager is small enough to be handheld. Built from easily obtainable materials for under $3,000.00, it contains no moving parts, so its durability is limited only by the ruggedness of the CCD detector. The reader is designed for quantitative detection of the emission of light or other indicia from a labeled biological sample. The present invention provides a small portable prototype reader capable of running on solar or battery pack for field diagnosis. The present invention is useful for clinical or triage setting for any biodetection scenario for capturing nucleic acids or proteins. Although its development is targeted towards microarray applications, it is also capable of imaging any type of thin fluorescent sample within standard wavelengths. Immediate applications include use in biodosimetry, pathogen analysis and environmental detection.

Forward detection is preferable to alternatives using dichroic mirrors for several reasons including cost, simplicity, and size. One specific benefit of using forward detection is the ability to easily change wavelengths. All of the filters and the LED are easily accessible, and exchanging the filters and LED does not affect the alignment (as would be the case with a dichroic mirror). This allows the device to be used for multiple applications, with different wavelengths beyond the initial experiments where Cy3 and Cy5 dyes were used. Additional implementations include snap-, screw-, or set-in filter and LED sets for quick interchangeability. Another implementation could include, but is not limited to, mechanical filter and LED wheels or mechanical filter wheels with a broadband light source such as a white light LED.

Figure 2:
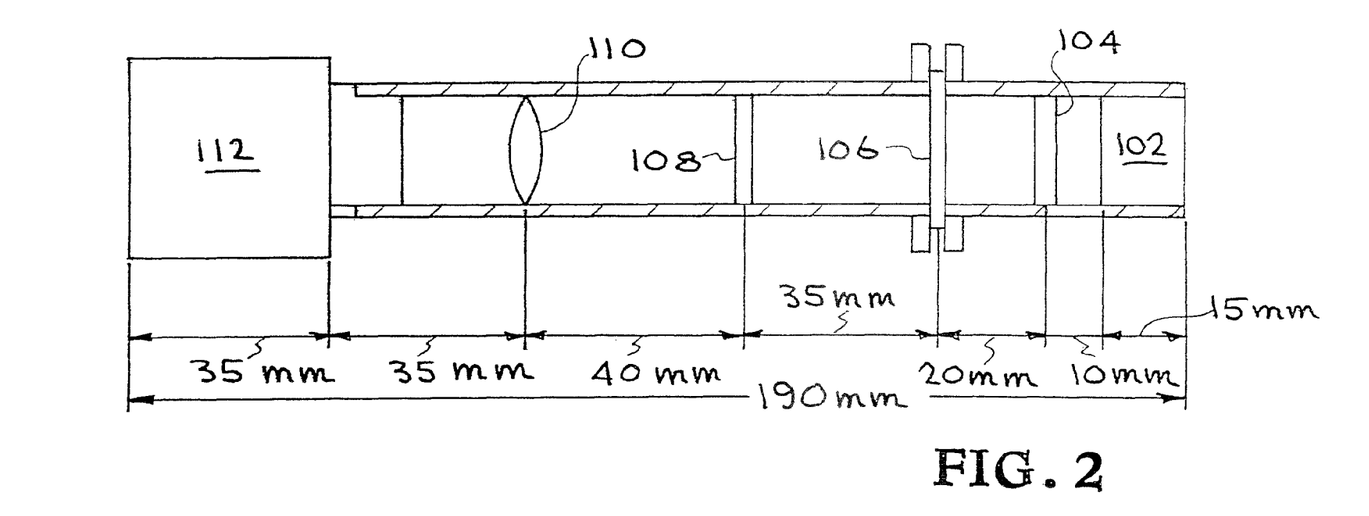
FIG. 2 is an optical layout of the hand-held microarray reader for biodetection.

Referring now to FIG. 2 an optical layout of the hand-held microarray reader for biodetection 100. The hand-held microarray reader for biodetection 100 includes the following structural elements: a high-powered LED 102, excitation filters 104, slide holder assembly 106, emission filters 108, lens 110, and camera 112. The hand-held microarray reader for biodetection 100 measures only 19 cm in length with a base of 6.5 cm×5 cm and is small enough to be handheld. The optical layout of the hand-held microarray reader for biodetection 100 includes the optical dimensions shown in FIG. 2. The width of the LED 102 is 15 mm. The width of the camera 112 is 35 mm. The excitation filters 104 are positioned 10 mm from the LED 102. The slide holder assembly 106 is positioned 20 mm from the excitation filters 104. The emission filters 108 are positioned 35 mm from the slide holder assembly 106. The lens 110 is positioned 40 mm from the emission filters 108. The camera 112 is positioned 35 mm from the lens 110.

Figure 3:
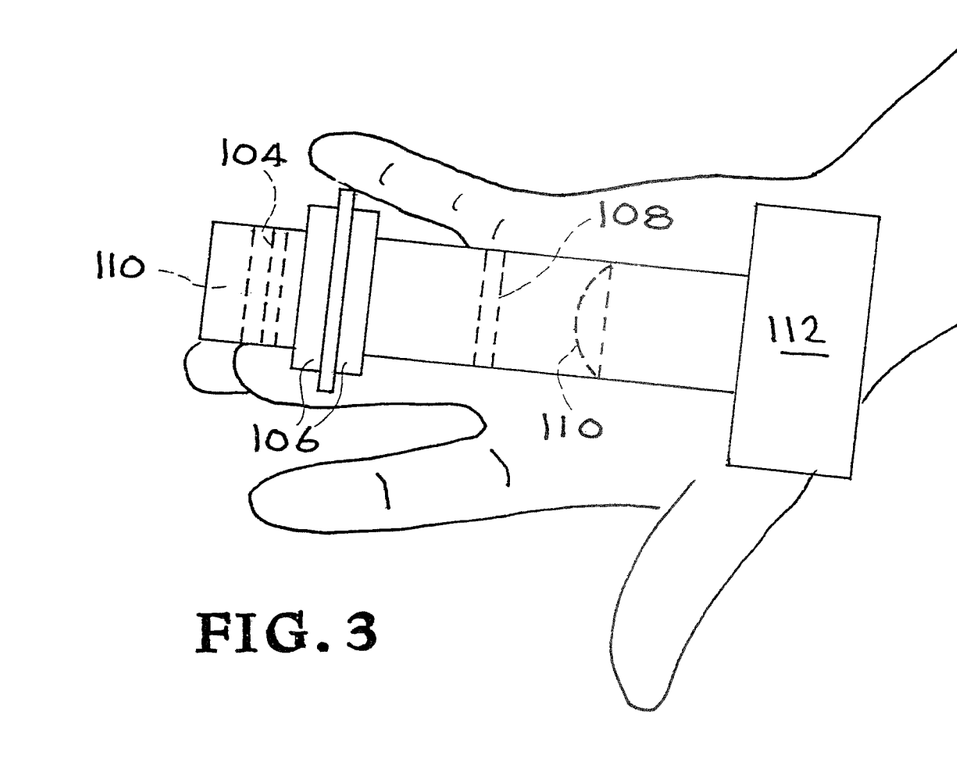
FIG. 3 illustrates the size of the hand-held microarray reader for biodetection.

Referring now to FIG. 3 an actual image of the hand-held microarray reader for biodetection 100 is shown. The hand-held microarray reader for biodetection 100 includes the following structural elements: a high-powered LED 102, excitation filters 104, slide holder assembly 106, emission filters 108, lens 110, and camera 112.

The hand-held microarray reader for biodetection 100 provides hand-held portable microarray reader based on LEDs, lens and CCD camera. Measuring only 19 cm in length with a footprint of 6.5 cm×5 cm, the imager is small enough to be handheld. Built from easily obtainable materials for under $3,000.00, it contains no moving parts, so its durability is limited only by the ruggedness of the CCD detector. The reader is designed for quantitative detection of the emission of light or other indicia from a labeled biological sample. The present invention provides a small portable fluorescent prototype reader capable of running on solar or battery pack for field diagnosis. The present invention is useful for clinical or triage setting for any biodetection scenario for capturing nucleic acids or proteins. Immediate applications for use in biodosimetry, pathogen analysis and environmental detection.

Figure 4:
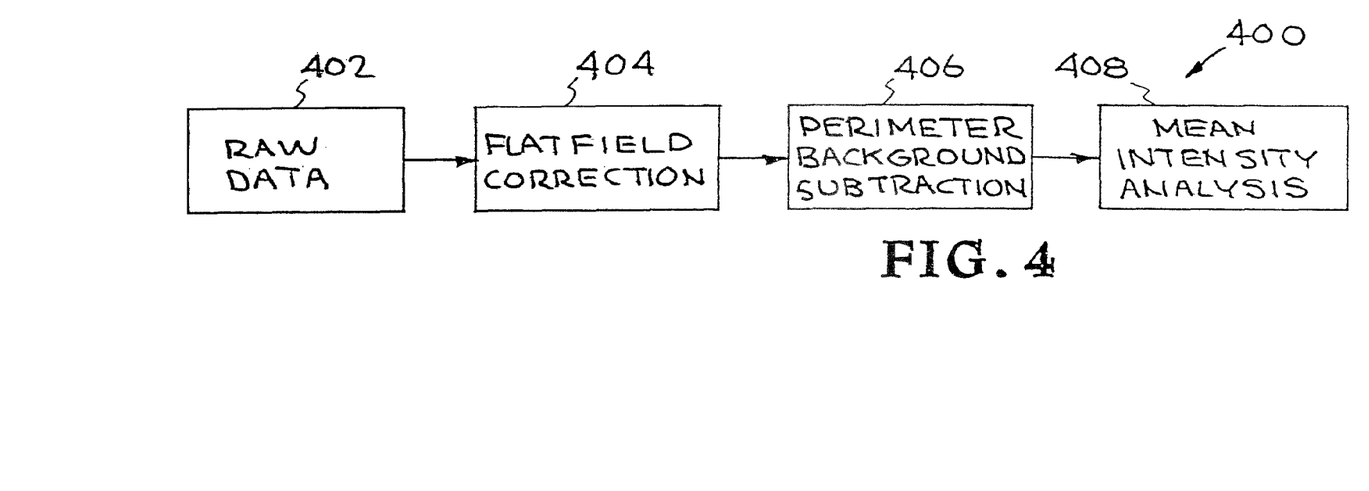
FIG. 4 is a flowchart depicting how a microarray image is processed.

Referring now to FIG. 4, a flowchart depicts how a microarray image is processed. The flowchart is designated generally by the reference numeral 400. Computer-based algorithms were implemented to turn the imaging system into a reader shown in flowchart 400. The first step, Raw Data 402, corrected for uneven light distribution from the LED. This simple step was applied to each image and verified by comparing two images recorded at different angles.

In the next step Flatfield Correction 404, each image was flatfield corrected using one of two equivalent methods. The first was to convert the images into MATLAB matrices using the 'imread' function in the Image Processing Toolbox. Each matrix entry i, j from the original image was divided by the corresponding entry i, j from the fluorescent slide's matrix. The new matrix was then scaled to the same mean value as the original image's matrix.

In the next step, Perimeter Background Subtraction 406, mean intensities of the spots and their perimeters were gathered, and background subtraction using this information was performed. These steps yielded the corrected mean spot intensities used for analysis, which were found to be comparable to the values obtained from a commercial laser scanner.

The next step, Mean Intensity Analysis 408. The new image was multiplied by the mean intensity of the calibration image, returning it to the same mean intensity as the original image. An important feature of microarray readers is the ability to detect the difference between two intensities that are within the same order of magnitude. For these types of applications where low SDs are important, multiple images with longer exposures are needed to improve signal-to-noise ratio. As mentioned above, brighter spots (close to the saturation value of the camera) were observed to have SDs that were relatively low compared to the mean intensity.

Referring now to FIGS. 5A, 5B, 5C, and 5D, a comparative analysis of the handheld reader's results with those of a traditional scanner is provided. Each graph was normalized so the brightest spots each had intensity values of 100. Error bars represent a total of two SDs for each spotting group. (FIG. 3A) Intensities of the PBS spots and the 10:1 printing ratio of Cy3 streptavidin are plotted. (FIGS. 5B & 5C) The 100:10:1 printing ratios are reflected in the fluorescence intensity ratios for both of these spotting groups. (FIG. 5D) The handheld scanner reaches its detection limit for the concentrations shown of anti goat IgG biotin where the SD is larger than the mean intensity value.

Figure 5A:
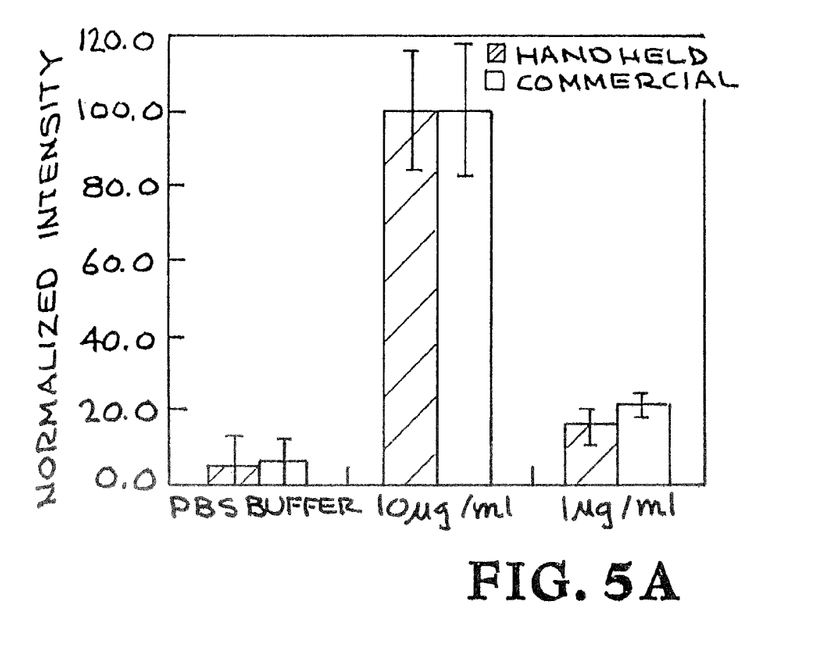
FIGS. 5A, 5B, 5C, and 5D provide a comparative analysis of the handheld reader's results with those of a traditional scanner.
Figure 5B:
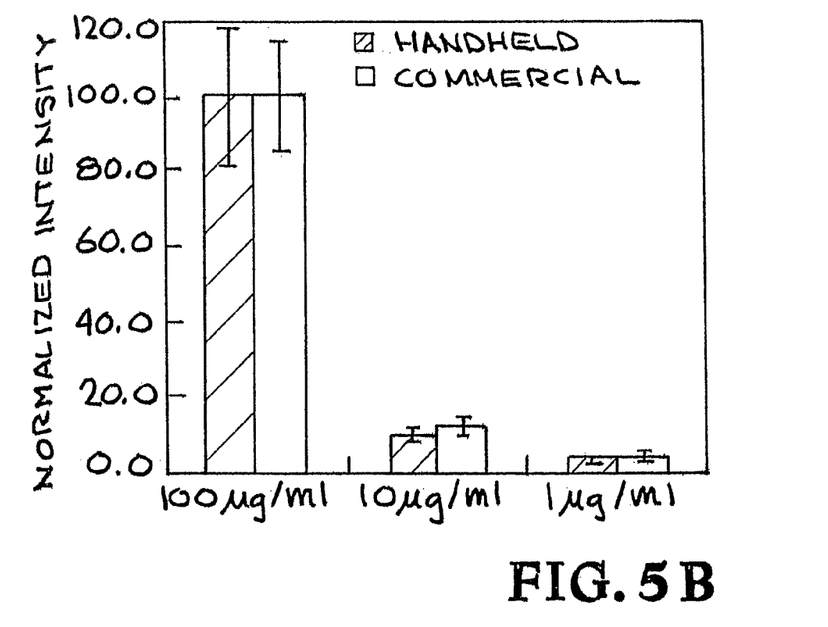
Figure 5C:
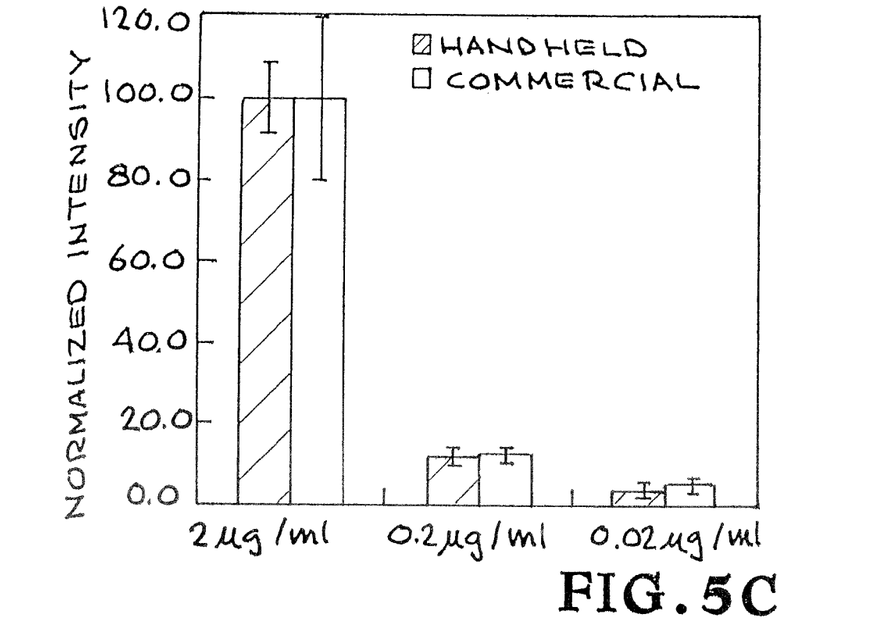
Figure 5D:
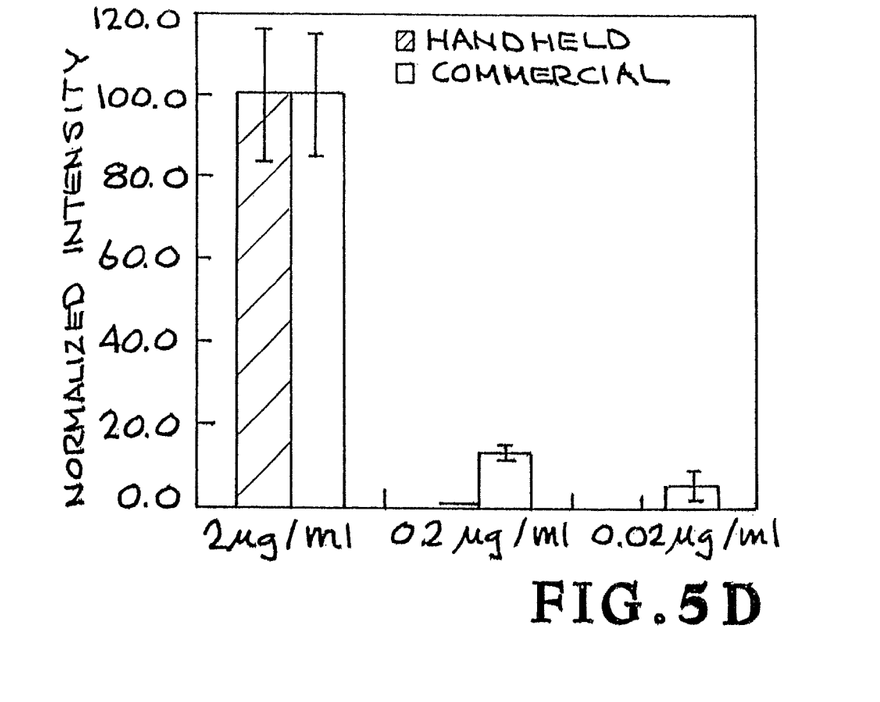

The intensity plots in FIGS. 5B, 5C clearly correlate with the expected spotting ratios. The detection limit of the reader for low concentrations with a 40 exposure time becomes evident in FIG. 5D, where the SD of the anti goat IgG biotin 0.02 μg/mL spots (SD=78) is larger than the mean intensity value (I=51) after background subtraction.

The SDs for the handheld reader, as a percentage of the correlated mean intensities, ranged from 9% to 183%, whereas the commercial scanner ranged from 10% to 116%. Looking at groups of spots with 3 orders of magnitude of detectable intensities, specifically the spots represented in FIG. 5A, 5C, the SDs were greatly reduced. For the handheld scanner, this narrows to 9% to 55% with a mean of 25% and the highest percentages at the weakest spots. For the scanner, the range is 14% to 40%, with a mean SD of 22%.

These results suggest that this microarray reader is an excellent replacement for several applications requiring multiple order-of-magnitude intensity detection. For a single exposure time, Applicants' device is able to detect intensities spanning three orders of magnitude, which is comparable to the commercial scanner used. By taking multiple images with different exposure times, the dynamic range can be further extended. For example, by taking three exposures at 10 ms, 1 s, and 100 s, a total of seven to nine orders of magnitude of intensity could reasonably be covered. This would require that spots be spaced far enough apart to avoid the overlap of saturated CCD pixels corresponding to bright spots with pixels corresponding to adjacent spots, which is easily accomplished with the large field of view of Applicants' device. For example, doubling the spot-to-spot distance to 500 μm would still allow detection of an array of 15×20 spots within a single image.

Figure 6A:
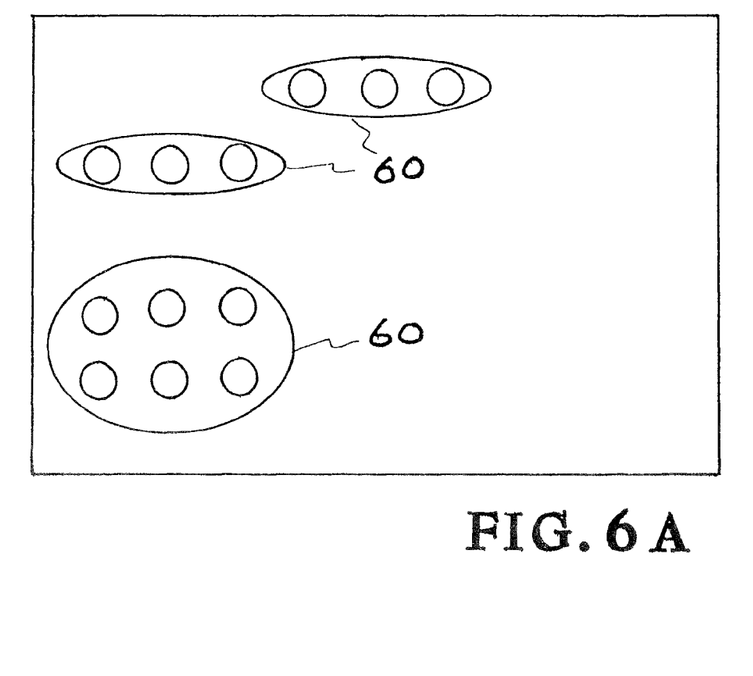
FIGS. 6A and 6B provide a comparison of scanned microarrays from the handheld reader and a commercial scanner, and 6C provides a legend of the samples scanned.
Figure 6B:
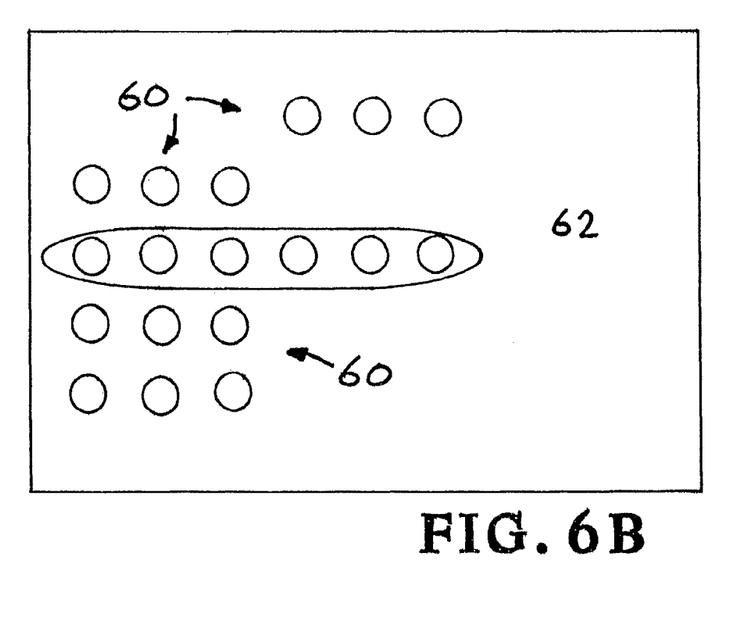
Figure 6C:
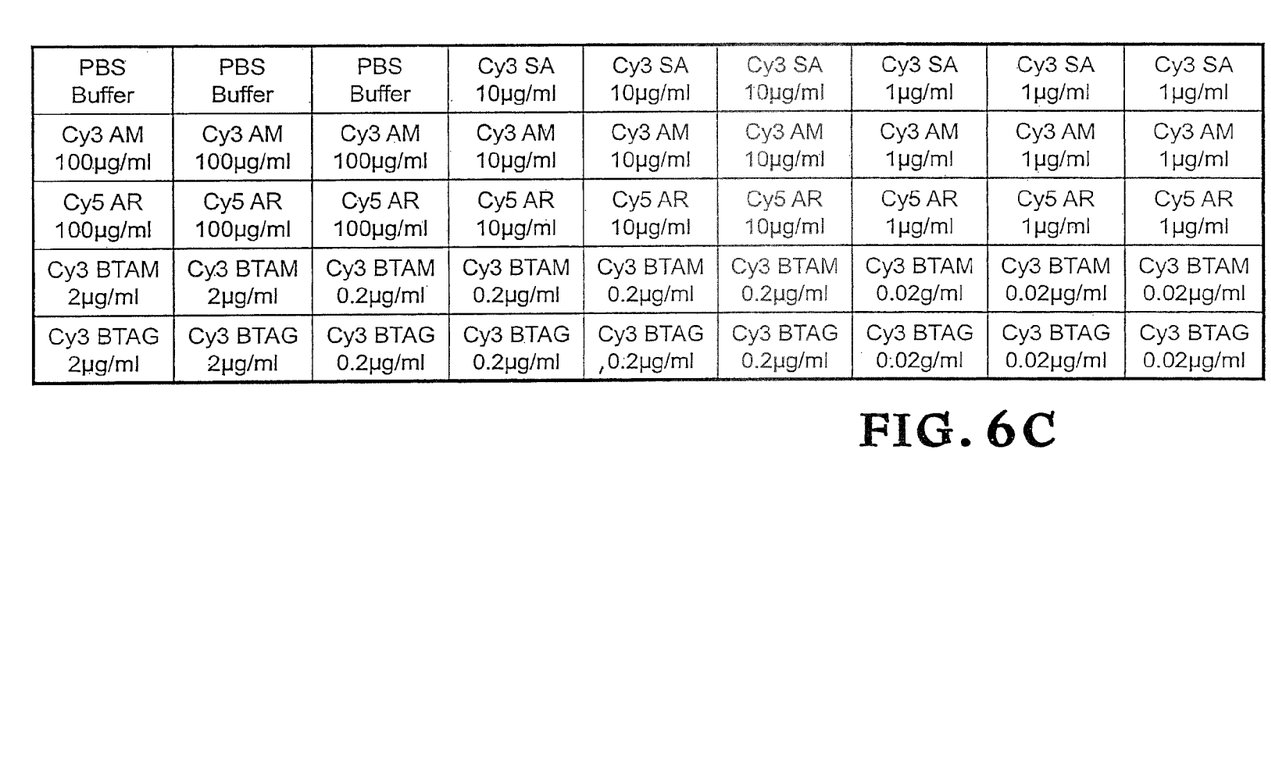

Referring now to FIGS. 6A, 6B and 6C. FIGS. 6A and 6B are illustrations of scanned images. FIG. 6A is the image taken with the hand-held imager of the present invention. FIG. 6B is the image taken by the commercial scanner Gemepix 4000B. In the composite false-color image from the scanner, the dots indicated by the numeral 60 are labeled with Cy3 and would appear green in the false-color image.

In FIG. 6A, the enclosed dots with the numeral 60 correspond to the dots also labeled 60 in FIG. 6B. In FIG. 6B, the enclosed series of dots with the referenced numeral 62 have been labeled with Cy5 and would appear red in the false-color image. The dots 62 of FIG. 6B are undetectable with the scanner of the present invention using the current filter setup. In FIG. 6C a legend of the protein and concentration used for each array spot. The layout of the chart matches the layout of the spots in the arrays shown B-PBS buffer, SA=streptavidin, AM=anti mouse, AR—anti rabbit, BTAM=anti mouse biotin, BTAG=anti goat biotin. The dye is spotted directly onto the array for the first three rows only. A later incubation step conjugates the dye to the biotin for the bottom two rows.

Reagents were spotted at concentrations shown in FIGS. 6A and 6B. PBS was printed as a negative control. One labeled peptide and four different antibodies were printed as positive controls: Cy3 streptavidin (Cy3 SA), Cy3 anti mouse IgG (Cy3 AM), anti mouse IgG biotin (BTAM), anti goat IgG biotin (BTAG) (Rockland Immunochemicals, Inc. Gilbertsville, Pa., USA), and Cy5 anti rabbit IgG (Cy5 AR) (Zymed Invitrogen, Carlsbad, Calif., USA). The antibodies were diluted in 2× Protein Arraying Buffer (Schleicher & Schuell, Whatman, Kent, UK) to a total volume of 15 μL in a 96-well titer plate.

Approximately 10 nL of each solution was printed on Corning GAPS II Slides (Invitrogen, Carlsbad, Calif., USA) using the OmniGrid Accent (Genomic Solutions, Ann Arbor, Mich., USA) arrayer. Slides were crosslinked for 5 mins using UV irradiation. Four subarrays were printed on each slide, and the spacing was 250 μm spot-to-spot both horizontally and vertically within each subarray. The array layout can be seen in FIG. 4C. Prior to use, the slides were blocked for 1 hour using PBS containing 1 mg/mL of BSA. The slides were then washed three times in 1×PBS containing Tween 20. For detection, a total of 800 μL of Cy3 SA in PBS was added to the array. The Cy3 SA interacts with the biotin to allow detection. After a 10 minute incubation period, slides were again washed three times for five minutes in 1×PBS before air drying.

Figure 7A:
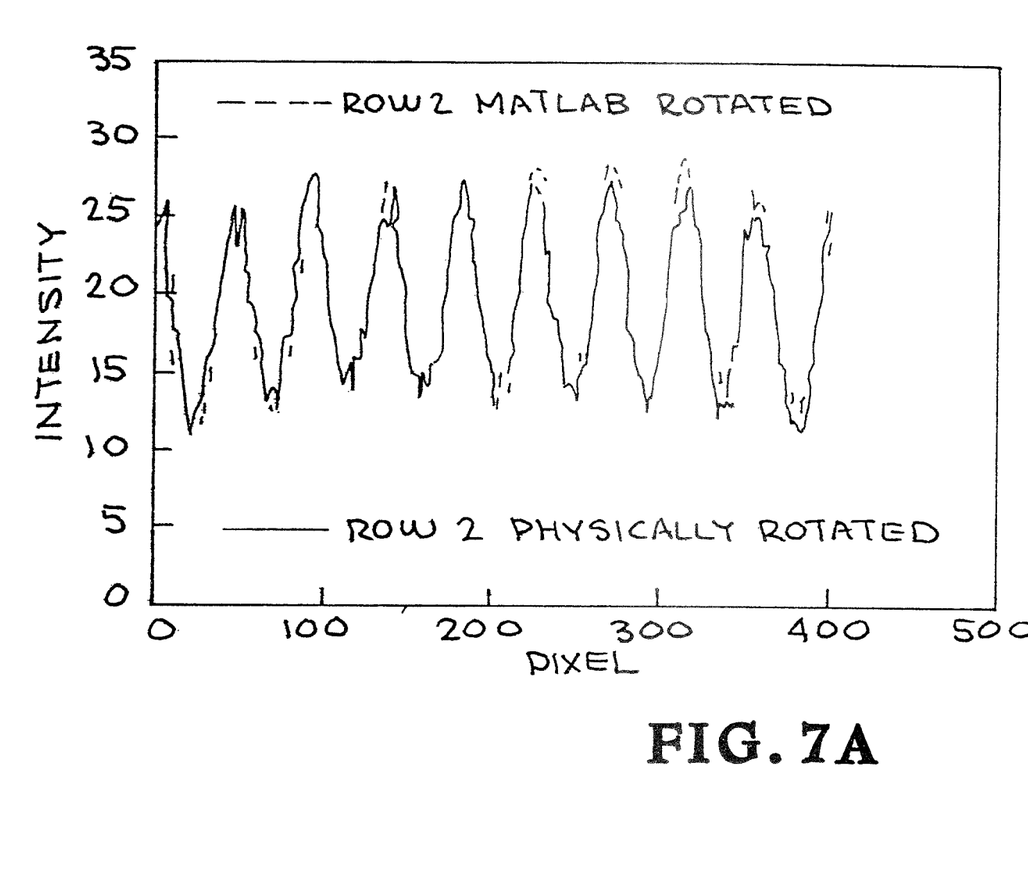
FIGS. 7A, 7B, and 7C show comparisons of row histograms of two images of the same array to validate the correction program.
Figure 7B:
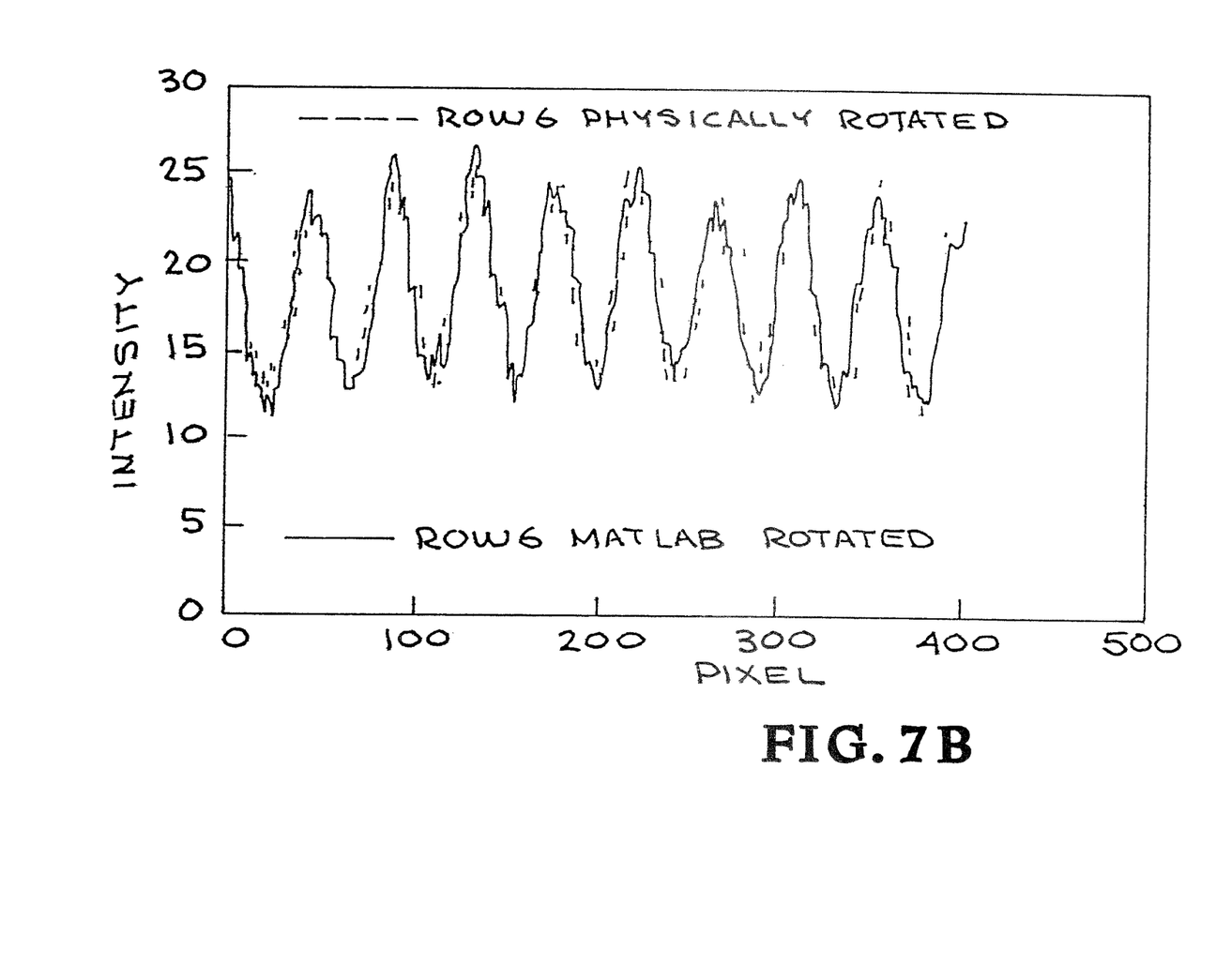
Figure 7C:
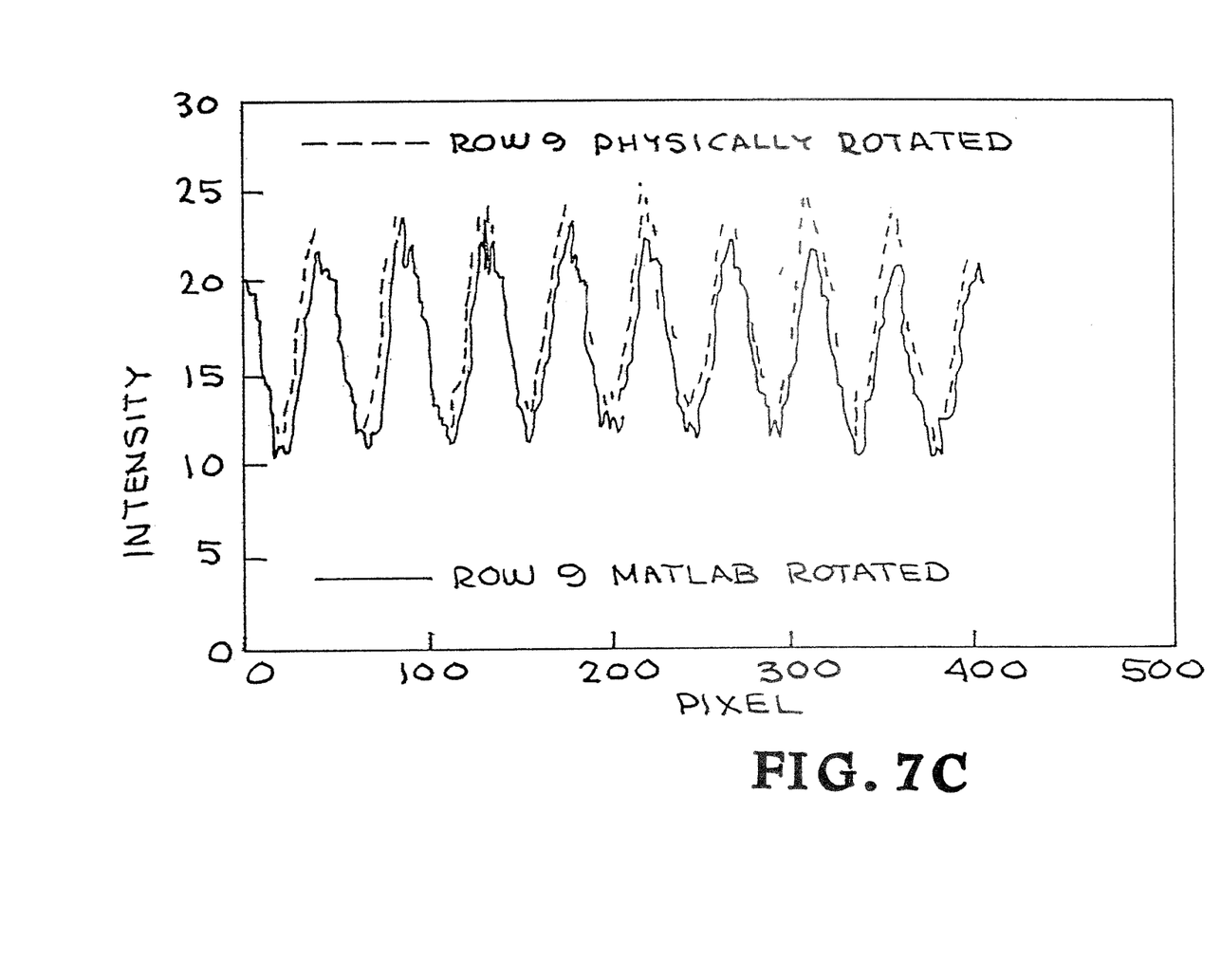

Referring now to FIGS. 7A, 7B, and 7C comparisons of row histograms of two images of the same array are shown. Dashed lines represent physically rotated arrays and solid lines represent computer rotated arrays. The agreement between the two histograms indicates a successful flatfield correction program.

Additional upgrades are possible to improve portability. First, a program automating all of the steps described above is needed, such as provided by the UCSF Spot program. With arrays in a fixed position relative to the detector, the same pixel numbers can be used every time to gather means and SDs, or object-recognition software can be used to select spot borders. The next optimization step is to reduce the number of separate wires required. Currently the LED is powered by a variable power supply, but it has also been successfully run off a pair of C batteries. Future designs could power both the LED and the camera (which currently requires a standard electrical outlet) through a USB connection. This would allow the device to be taken to remote areas, requiring only a standard laptop to both power the device and process the images. The programs required to analyze the image could all be included on a chip, along with application-specific programs, and wired directly into the device.

This would transition the handheld microarray imager into a fully contained, highly specialized handheld microarray reader. Furthermore, the cost of the reader can be reduced much below the current $3,000 figure. By using commercial rather than research products, components such as the optical tube or the camera can be acquired at a much lower cost.

EXAMPLES

Handheld microarray imager
Imager structure
A Thor Labs 25.4 mm optical tube encloses the entire device, with the exception of the CCD camera, thus blocking outside light from interfering with fluorescence detection. The slide holder is a Thor Labs cage assembly, with two rods supporting the slide from below and the cage assembly plates sandwiching the slide to hold it in place.

Light Source
At one end of the tube, an ultra-bright Luxeon® Star with Optics LED, powered at 3.3 V, provides illumination to back illuminate a standard microscope slide. The light emitted has a peak wavelength of 530 nm with a range of 520-550 nm, and the power was measured to be approximately 80 mW.

Filters

A set of two 532/10 nm filters (Chroma Technology Corporation, Vt., USA) narrows the excitation wavelength range to 527-537 nm. The excitation light and the fluorescence signal coming from the sample slide passes through three more filters. The first two filters, a 572 nm longpass (Chroma) and a 590 nm longpass (Andover Corporation, NH, USA), block the excitation wavelengths. The third filter, a 592/100 nm bandpass filter (Chroma), stops the infrared signature from the LED from reaching the camera.

Lens

The tube lens used has a 25.4 mm focal length and diameter from Thor Labs. The inherent NA is 0.45, while the NA for collection geometry is 0.17. Because the light from the sample is not collimated, the distance between the sample and the lens is much greater than the focal distance, resulting in the lower NA.

Camera

The camera, an LU130M (Lumenera Corporation, Ottawa, Canada), has a ½" monochromatic chip with a pixel size of 4.65 square μm and a 60 dB dynamic range. The manufacturer lists a dark count of 2 electrons (per pixel per second) at 25° C. with a readout noise of 8 electrons, and a quantum efficiency of 40% at 500 nm.

Microarray Manufacturing

Comparative Analysis Slides

Reagents were spotted at concentrations shown in FIG. 4. PBS was printed as a negative control.

One labeled peptide and four different antibodies were printed as positive controls: Cy3 streptavidin (Cy3 SA), Cy3 anti mouse IgG (Cy3 AM), anti mouse IgG biotin (BTAM), anti goat IgG biotin (BTAG) (Rockland Immunochemicals, Inc. Gilbertsville, Pa., USA), and Cy5 anti rabbit IgG (Cy5 AR) (Zymed Invitrogen, Carlsbad, Calif., USA). The antibodies were diluted in 2× Protein Arraying Buffer (Schleicher & Schuell, Whatman, Kent, UK) to a total volume of 15 μL in a 96-well titer plate.

Approximately 10 nL of each solution was printed on Corning GAPS II Slides (Invitrogen, Carlsbad, Calif., USA) using the OmniGrid Accent (Genomic Solutions, Ann Arbor, Mich., USA) arrayer. Slides were crosslinked for 5 mins using UV irradiation. Four subarrays were printed on each slide, and the spacing was 250 μm spot-to-spot both horizontally and vertically within each subarray. The array layout can be seen in FIG. 4C. Prior to use, the slides were blocked for 1 hour using PBS containing 1 mg/mL of BSA. The slides were then washed three times in 1×PBS containing Tween 20. For detection, a total of 800 μL of Cy3 SA in PBS was added to the array. The Cy3 SA interacts with the biotin to allow detection. After a 10 minute incubation period, slides were again washed three times for five minutes in 1×PBS before air drying.

Flatfield Correction Slide

The flatfield correction slide was prepared in a manner similar to that of the comparative analysis slides. ATM synthetic peptide was used, and 10×10 spot subarrays were printed in a 2 column, 4 row format. Spacing of spots in both the vertical and horizontal position is 300 microns, except for the first array which has spacing of 500 vertically and 300 horizontally.

Flatfield Correction:

Each image was flatfield corrected using one of two equivalent methods. The first was to convert the images into MATLAB matrices using the 'imread' function in the Image Processing Toolbox.

Each matrix entry i, j from the original image was divided by the corresponding entry i, j from the fluorescent slide's matrix. The new matrix was then scaled to the same mean value as the original image's matrix. FIG. 5 shows a comparison of an original and corrected image, including the divided difference and subtracted difference. The final matrix was converted into a bitmap image and saved as a new file. Alternatively, the flatfield correction could be done using Image J. The original image was divided by the calibration image using the 'Image Calculator' function. The new image was then multiplied by the mean intensity of the calibration image, returning it to the same mean intensity as the original image. To test this method, two images were taken of the same array. The slide was physically rotated 90° between the two pictures, and a third image was taken of the calibration slide. Each of the two array images was flatfield corrected using the MATLAB program. The second image was rotated to match the orientation of the first, and a defect in the array was used to confirm the match. The 'Plot Profile' feature of ImageJ measured the intensity along rows in the microarray. The data was extracted to Microsoft Excel, and the intensities were normalized to a mean value of one. The normalized intensities of one row on the first image were plotted versus the pixel number, and the same data from the second image was superimposed on it. Three of ten rows were analyzed in this manner.

Comparative Protein Array Analysis

Using the handheld microarray reader, images with 40 second exposure times were recorded of each of the total of 8 arrays printed on the two slides described in Section 3.2. The exposure time was chosen to avoid saturation of the camera and also to capture a range of intensities spanning several orders of magnitude. Images were then Hatfield corrected and background subtracted.

Image analysis was performed using ImageJ. A circle of fixed radius was hand-centered on each spot in the arrays, with the radius chosen to encompass the largest spot. The mean intensities and SDs of each spot were measured, then recorded and analyzed in an Excel spreadsheet.

A GenePix 4,000 B commercial scanner (Axon Instruments, Union City, Calif., USA) was used to take scans of the same slides. The PMT gain was set to 400 for Cy3 (532 nm) and 600 for Cy5 (635 nm). The included software provided the mean intensities and SDs used in this analysis.

With each antibody mixture spotted in triplicate per array, this yielded a total of 18 spots per antibody type and concentration to be analyzed. The SDs shown in Applicants' results (the error bars in FIG. 3) were calculated from these 18 data points. Only three out of four arrays per slide were analyzed.

The present invention provides a relatively low-cost portable reader capable of detecting intensities over multiple orders of magnitude. Although other handheld imagers have been developed, to Applicants' knowledge no direct comparison with traditional microarray scanners has been previously reported.

With Applicants' device, the mean SD in intensity detection was only 25%, compared to 22% for a commercial laser seamier. This high degree of comparability makes it a reliable choice for POC testing. Also amenable to a POC setting, the device is small enough to be handheld, measuring only 19 cm in length.

It has the potential to be powered and run entirely by a laptop or to be self-contained with a software chip and battery. In addition the device could be quickly adapted for a variety of assay formats, including lateral flow assays.

Because it is powered by an LED rather than a laser, and the filters are easily accessible, Applicants' reader also is flexible in its excitation and emission spectra. The ability to use a variety of dyes makes Applicants' reader applicable to both the clinical and laboratory setting, and highly adaptable for many microarray based tests. Also unlike previous handheld imagers, the digital format of Applicants' imager allows the information to be directly recorded on a computer or other electronic device for quick analysis. In the future Applicants' device could potentially send a diagnosis directly to a doctor's or technician's PDA, dramatically increasing the ability to treat a patient without delay.

Additional information about Applicants' invention is provided in the article, "An Adaptable, Portable Microarray Reader for Biodetection," by Deanna L. Thompson, Francesca Pearson, Cynthia Thomas, Rupa Rao, Dennis Matthews, Joanna S. Albala, Sebastian Wachsmann-Hogiu, and Matthew A. Coleman, in the journal *Sensors* 2009, 9, 2524-2537. The article, "An Adaptable, Portable Microarray Reader for Biodetection," by Deanna L. Thompson, Francesca Pearson, Cynthia Thomas, Rupa Rao, Dennis Matthews, Joanna S. Albala, Sebastian Wachsmann-Hogiu, and Matthew A. Coleman, in the journal *Sensors* 2009, 9, 2524-2537 is incorporated herein in its entirety for all purposes.

While the invention may be susceptible to various modifications and alternative forms, specific embodiments have been shown by way of example in the drawings and have been described in detail herein. Applicants' imager was designed for and used with slides, but could be used to image almost any thin fluorescent sample (thin enough for the back illumination to still be effective but not block too much emission), such as cuvettes, coverslips, or shaped plastic. The slide-holder assembly as-is would work best with a slide, but can change the thickness of the sample it is holding so it is not limited to traditional slides. Also, Applicants' slide doesn't have to include only microarrays—it could be any pattern or many other sample types, including cells.

The wavelengths of Applicants' LED and filters were just for this prototype. Any color LED can be combined with the appropriate filters in order to image a different fluorophore. Applicants used Cy3, but almost any fluorophore (such as YFP, alexa568, Cy5, etc.) could be used and detected by our system by changing the LED and filters. An easy-to-change system where LEDs and filters unscrew or disconnect easily and are replaced screwing in or otherwise connecting different wavelength filters and LEDs could enable the reader to be used at different wavelengths within a few seconds or minutes. Alternately, a manual or automated filter and LED wheel set could allow the user to change wavelengths by simply rotating the wheel, changing which filters and LED are in the optical path and which filters and LED are not actively in use.

Applicants' USB connection to the computer could also be firewire, SATA, eSATA, or any other data transfer mechanism, including wireless transmissions to near or far locations.

Applicants' device could include a chip to do all of the analysis on the device itself, without needing a laptop connection. This would require inclusion of software such as object recognition and an automation of data processing algorithms included in this patent. It could also include application-specific data processing such as translating intensity values to a clinical diagnosis. The output could be through transmission to a laptop, or directly displayed on the device, such as through selective illumination of colored LEDs.

It should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A hand-held portable microarray reader apparatus for analyzing a sample, comprising:
a high-powered light-emitting diode,
an excitation filter,
a sample holder,
an emission filter,
a lens, and
a camera; wherein said high-powered light-emitting diode, said excitation filter, said sample holder, said emission filter, said lens, and said camera are aligned in an envelope so that
said high-powered light-emitting diode emits excitation light,
said excitation filter is positioned to receive said excitation light,
said sample holder is located in said envelope for positioning said sample to receive said excitation light from said excitation filter,
said emission filter is positioned to receive said excitation light from said sample holder,
said lens is positioned to receive said excitation light from said emission filter, and
said camera is positioned to receive said excitation light from said lens.

2. The hand-held portable microarray reader apparatus for analyzing a sample of claim 1 including a USB connection on said camera and a laptop computer connected to said camera through said USB connection.

3. The hand-held portable microarray reader apparatus for analyzing a sample of claim 1 wherein said camera is a CCD camera.

4. The hand-held portable microarray reader apparatus for analyzing a sample of claim 1 wherein said high-powered light-emitting diode is positioned to provide illumination to back illuminate said sample holder with said excitation light.

5. The hand-held portable microarray reader apparatus for analyzing a sample of claim 1, wherein said high-powered light-emitting diode, said an excitation filter, said sample holder, said emission filter, said lens, and said camera are positioned relative to each other such that the hand-held portable microarray reader apparatus for analyzing a sample fits within an envelope of 20 cm by 7 cm by 5 cm or smaller.

6. The hand-held portable microarray reader apparatus for analyzing a sample of claim 5, wherein said an excitation filter, said sample holder, said emission filter, said lens, and said camera are located relative to each other such that the hand-held portable microarray reader apparatus for analyzing a sample fits within an envelope of 20 cm by 7 cm by 5 cm or smaller and wherein said excitation filter is located 10 mm from said high-powered light-emitting diode, wherein said slide holder assembly and said slide are located 20 mm from said excitation filter, wherein said emission filter is located 35 mm from said sample holder, wherein said lens is located 40 mm from said emission filter, wherein said camera is located 35 mm from said lens.

7. The hand-held portable microarray reader apparatus for analyzing a sample of claim 1 wherein said high-powered light-emitting diode is an ultra-bright LED, powered at 3.3 V, with a peak wavelength of 530 nm with a range of 520-550 nm, and the power being approximately 80 mW.

8. The hand-held portable microarray reader apparatus for analyzing a sample of claim 1 wherein said camera has a pixel size of 4.65 square µm and a 60 dB dynamic range.

9. The hand-held portable microarray reader apparatus for analyzing a sample of claim 7 wherein said camera has a dark count of 2 electrons per pixel per second at 25° C. with a readout noise of 8 electrons, and a quantum efficiency of 40% at 500 nm.

10. A hand-held portable microarray reader apparatus for analyzing a sample, comprising:
a high-powered light-emitting diode that emits excitation light,
an excitation filter positioned to receive said excitation light,
a sample holder for positioning said sample to receive said excitation light from said excitation filter,
an emission filter positioned to receive said excitation light from said sample holder,
a lens positioned to receive said excitation light from said emission filter, and
a camera positioned to receive said excitation light from said lens,
wherein said high-powered light-emitting diode, said an excitation filter, said sample holder, said emission filter, said lens, and said camera are positioned relative to each other such that the hand-held portable microarray reader apparatus for analyzing a sample fits within an envelope of 20 cm by 7 cm by 5 cm or smaller.

11. The hand-held portable microarray reader apparatus for analyzing a sample of claim 10, wherein said excitation filter, said sample holder, said emission filter, said lens, and said camera are located relative to each other such that the hand-held portable microarray reader apparatus for analyzing a sample fits within an envelope of 20 cm by 7 cm by 5 cm or smaller and wherein said excitation filter is positioned 10 mm from said high-powered light-emitting diode, wherein said sample holder assembly and said slide are positioned 20 mm from said excitation filter, wherein said emission filter is positioned 35 mm from said sample holder assembly, said lens is positioned 40 mm from said emission filter, and wherein said camera is positioned 35 mm from said lens.

12. A hand-held portable microarray reader apparatus for analyzing a sample, comprising:
a high-powered light-emitting diode that emits excitation light;
an excitation filter positioned to receive said excitation light;
a slide;
a slide holder assembly for positioning said slide to receive said excitation light from said excitation filter, wherein said high-powered light-emitting diode is positioned to provide illumination to back illuminate said slide with said excitation light;
an emission filter positioned to receive said excitation light from said slide;
a lens positioned to receive said excitation light from said emission filter; and
a CCD camera positioned to receive said excitation light from said lens.

13. A hand-held portable microarray reader apparatus for analyzing a sample, comprising:
a high-powered light-emitting diode that emits excitation light, wherein said high-powered light-emitting diode is an ultra-bright LED, powered at 3.3 V, with a peak wavelength of 530 nm with a range of 520-550 nm, and the power being approximately 80 mW;
an excitation filter positioned to receive said excitation light;
a slide;
a slide holder assembly for positioning said slide to receive said excitation light from said excitation filter, wherein said high-powered light-emitting diode is positioned to provide illumination to back illuminate said slide with said excitation light;
an emission filter positioned to receive said excitation light from said slide;
a lens positioned to receive said excitation light from said emission filter; and
a CCD camera positioned to receive said excitation light from said lens.

14. A hand-held portable microarray reader apparatus for analyzing a sample, comprising:
a high-powered light-emitting diode that emits excitation light, wherein said high-powered light-emitting diode is an ultra-bright LED, powered at 3.3 V, with a peak wavelength of 530 nm with a range of 520-550 nm, and the power being approximately 80 mW;
an excitation filter positioned to receive said excitation light;
a slide;
a slide holder assembly for positioning said slide to receive said excitation light from said excitation filter, wherein said high-powered light-emitting diode is positioned to provide illumination to back illuminate said slide with said excitation light;
an emission filter positioned to receive said excitation light from said slide;
a lens positioned to receive said excitation light from said emission filter; and
a CCD camera positioned to receive said excitation light from said lens, wherein said CCD camera has a dark count of 2 electrons per pixel per second at 25° C. with a readout noise of 8 electrons, and a quantum efficiency of 40% at 500 nm.

15. The hand-held portable microarray reader apparatus for analyzing a sample of claim 14,
wherein said excitation filter is positioned 10 mm from said high-powered light-emitting diode,
wherein said slide holder assembly and said slide are positioned 20 mm from said excitation filter,
wherein said emission filter is positioned 35 mm from said slide holder assembly and said slide,
wherein said lens is positioned 40 mm from said emission filter,
wherein said CCD camera is positioned 35 mm from said lens.

16. The hand-held portable microarray reader apparatus for analyzing a sample of claim 14 including a USB connection on said CCD camera and a laptop computer connected to said CCD camera through said USB connection.

* * * * *